(12) United States Patent
Chen

(10) Patent No.: US 9,597,178 B2
(45) Date of Patent: Mar. 21, 2017

(54) AURICULAR IMPLANT

(71) Applicant: SHAWHAN BIOMEDICAL CO., Taipei (TW)

(72) Inventor: ZungChung Chen, Taipei (TW)

(73) Assignee: SHAWHAN BIOMEDICAL CO. (TW)

( * ) Notice: Subject to any disclaimer, the term of this patent is extended or adjusted under 35 U.S.C. 154(b) by 167 days.

(21) Appl. No.: 14/718,660

(22) Filed: May 21, 2015

(65) Prior Publication Data

US 2015/0250586 A1 Sep. 10, 2015

Related U.S. Application Data

(63) Continuation-in-part of application No. 14/154,157, filed on Jan. 13, 2014, now abandoned.

(30) Foreign Application Priority Data

Jun. 5, 2013 (TW) .............................. 102119987 A

(51) Int. Cl.
*A61F 2/18* (2006.01)
*A61F 2/00* (2006.01)
*A61F 11/00* (2006.01)

(52) U.S. Cl.
CPC .............. *A61F 2/18* (2013.01); *A61F 2/0059* (2013.01); *A61F 11/004* (2013.01); *A61F 2002/183* (2013.01); *A61F 2220/0075* (2013.01)

(58) Field of Classification Search
CPC .... A61F 2/18; A61F 2002/183; A61F 2/0059; A61F 11/004
See application file for complete search history.

(56) References Cited

U.S. PATENT DOCUMENTS

| | | | |
|---|---|---|---|
| 3,257,668 A * | 6/1966 | Braley | ...................... A61F 2/18 623/10 |
| 5,433,748 A * | 7/1995 | Wellisz | ...................... A61F 2/18 623/10 |
| 5,876,447 A | 3/1999 | Arnett | |
| 6,277,150 B1 | 8/2001 | Crawley et al. | |
| 6,402,782 B1 * | 6/2002 | Sibbald et al. | ........ H04R 29/00 623/10 |
| 2005/0131527 A1 | 6/2005 | Pathak et al. | |
| 2010/0023124 A1 | 1/2010 | Xu et al. | |
| 2011/0264236 A1 | 10/2011 | Bassett et al. | |
| 2014/0364946 A1 | 12/2014 | Chen | |

* cited by examiner

*Primary Examiner* — Thomas J Sweet
*Assistant Examiner* — Daniel Bissing
(74) *Attorney, Agent, or Firm* — Bacon & Thomas, PLLC

(57) ABSTRACT

Disclosed herein is an auricular implant, comprising an auricular base and a supporting member. The auricular base has a first side and a second side opposite to the first side, wherein the first side thereof is disposed with a position unit. The supporting member having a thickness and a recess, wherein the position unit of the auricular base is disposed in the recess of the supporting member to adhere the supporting member to the first side of the auricular base for forming a stereoscopic disk-like structure.

18 Claims, 13 Drawing Sheets

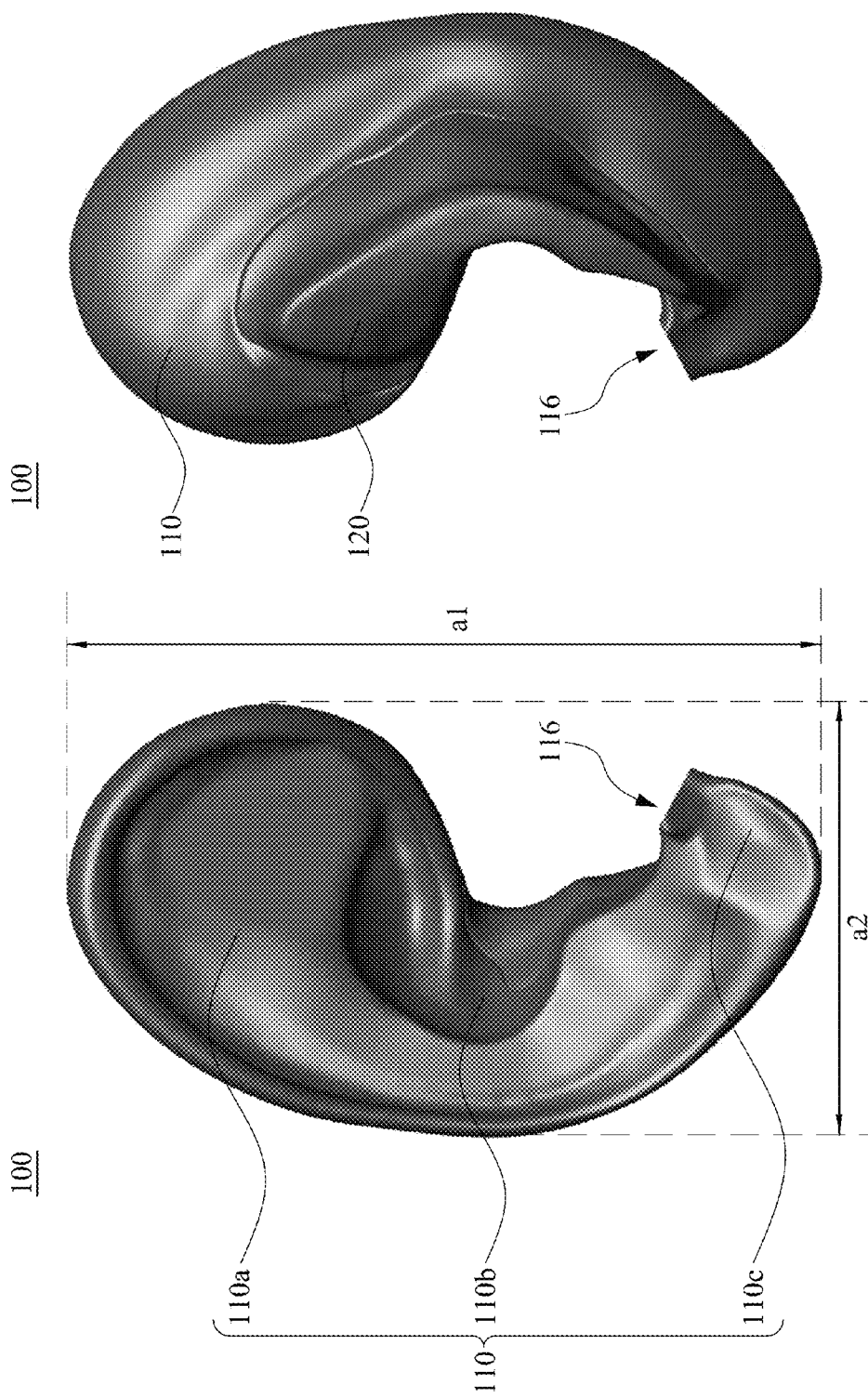

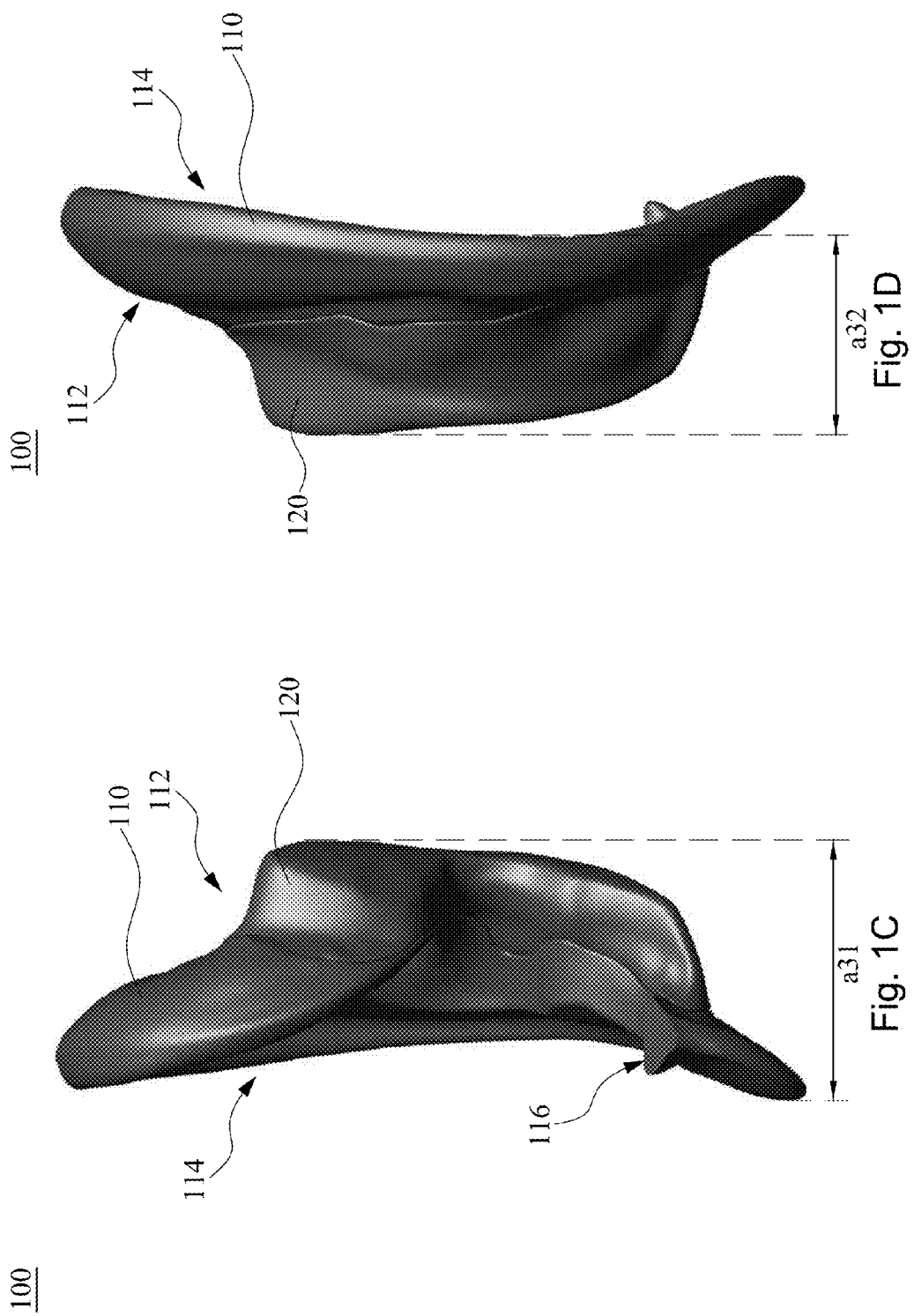

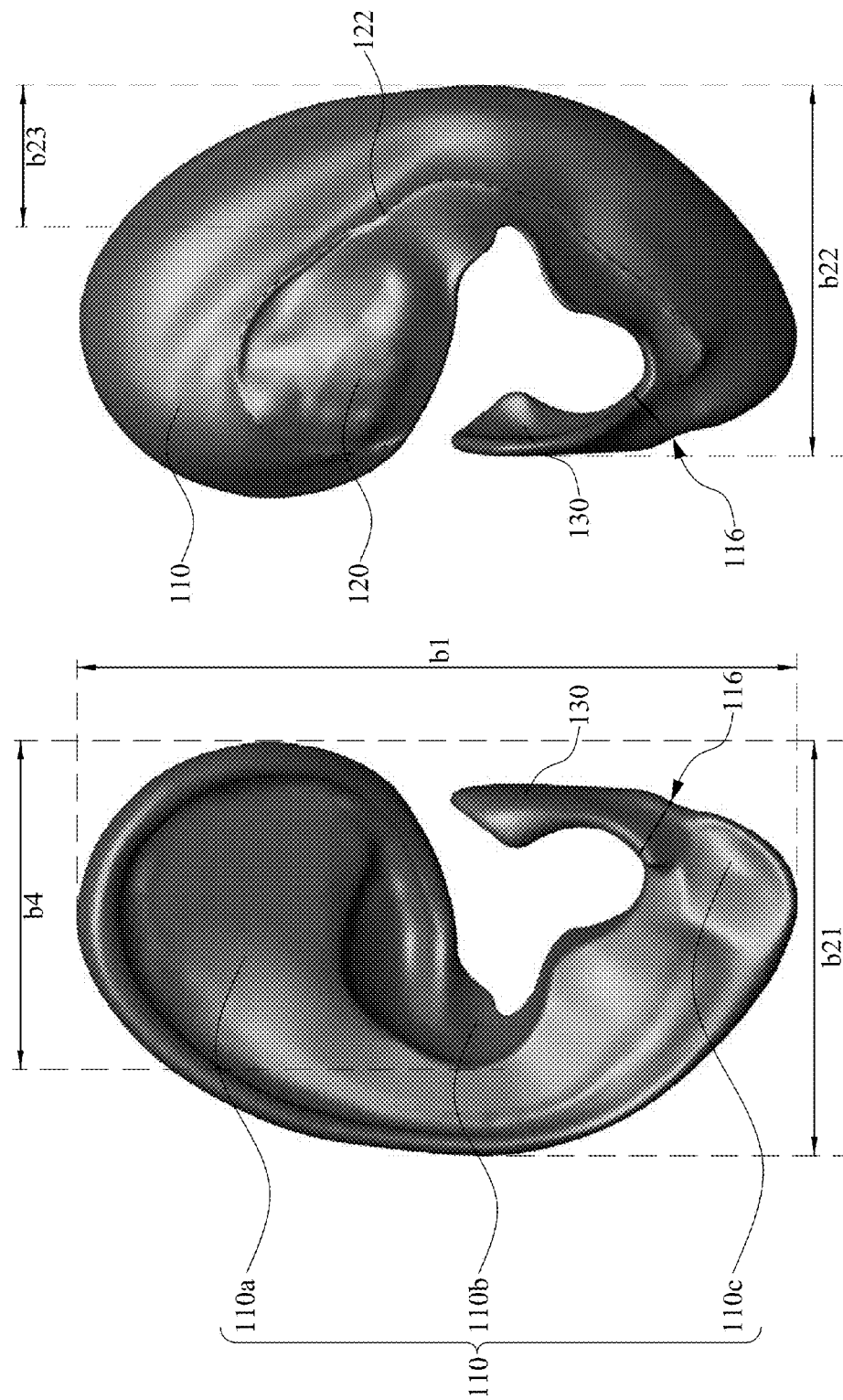

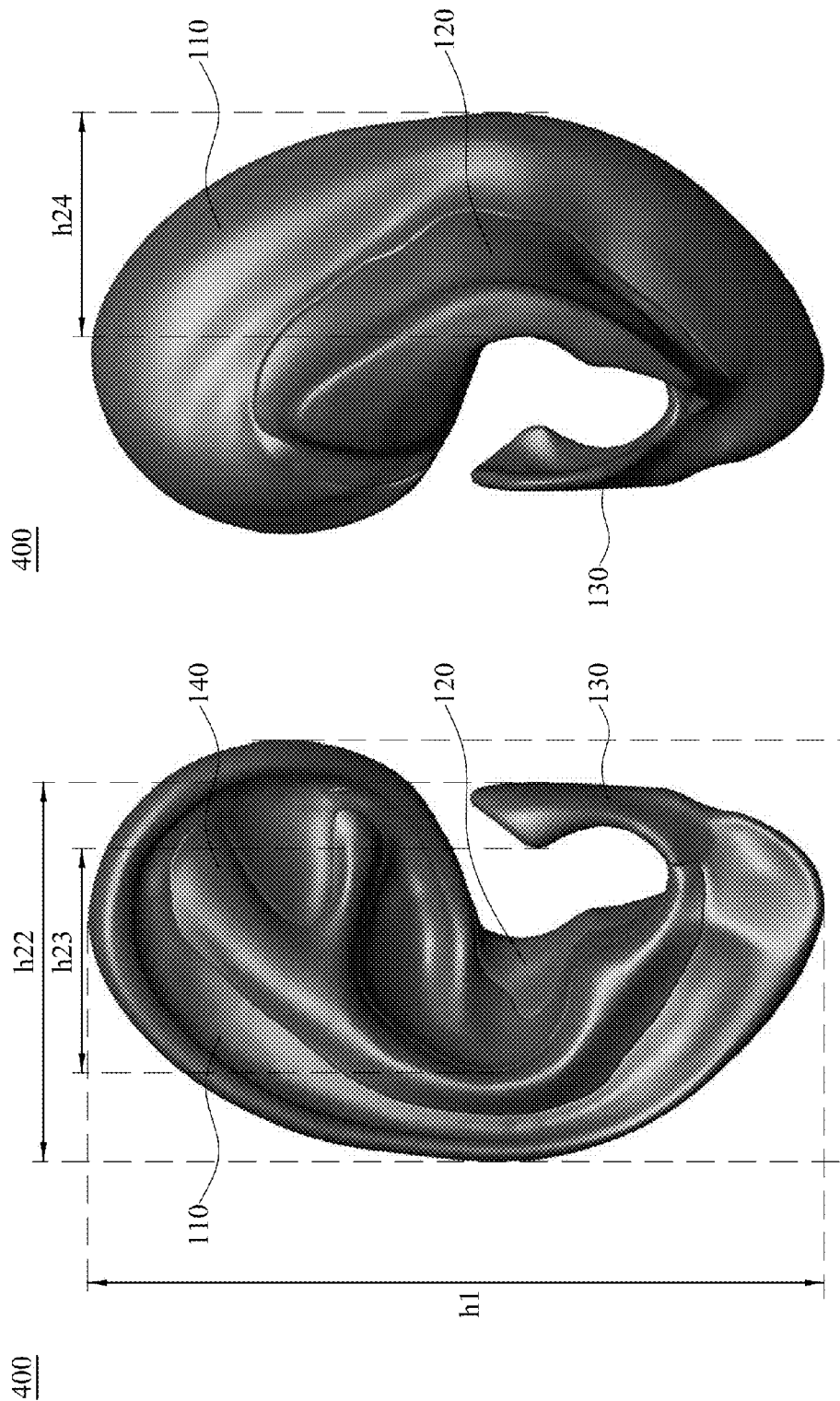

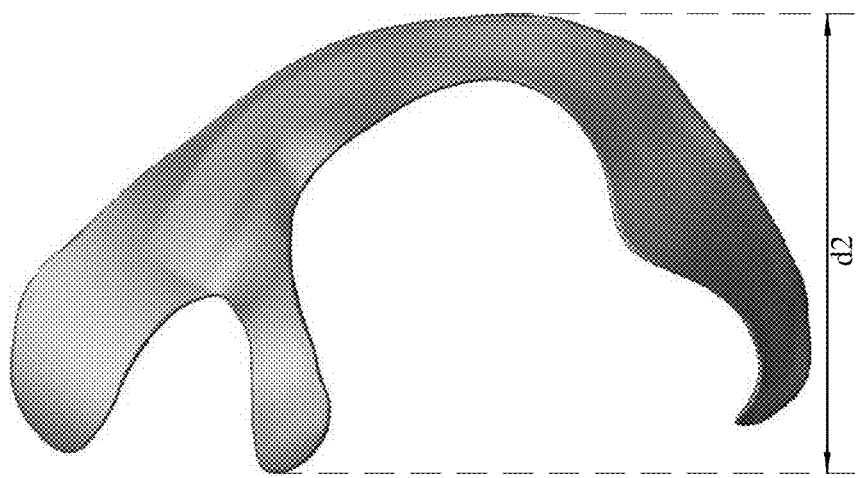
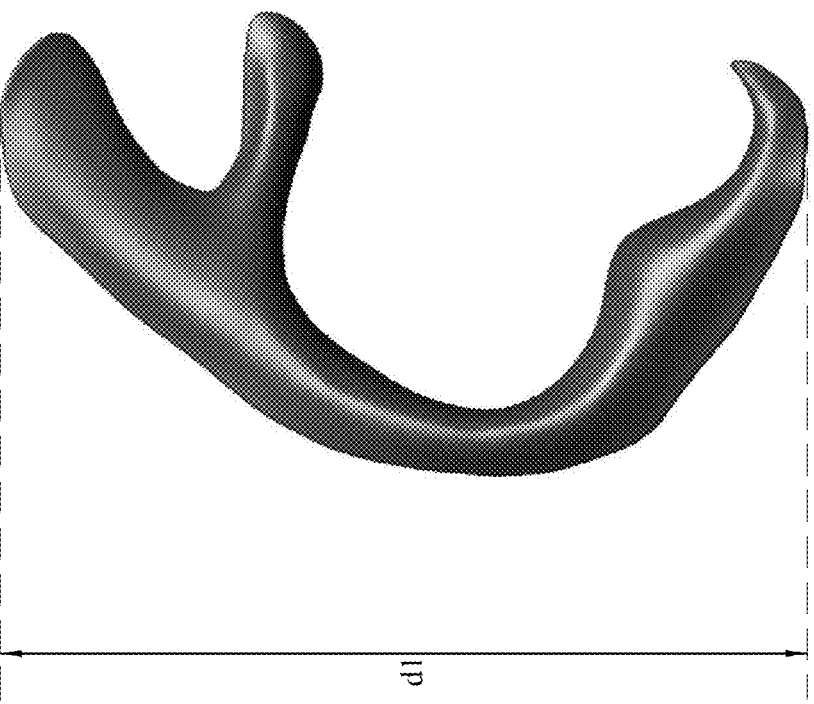
Fig. 5B
Fig. 5A

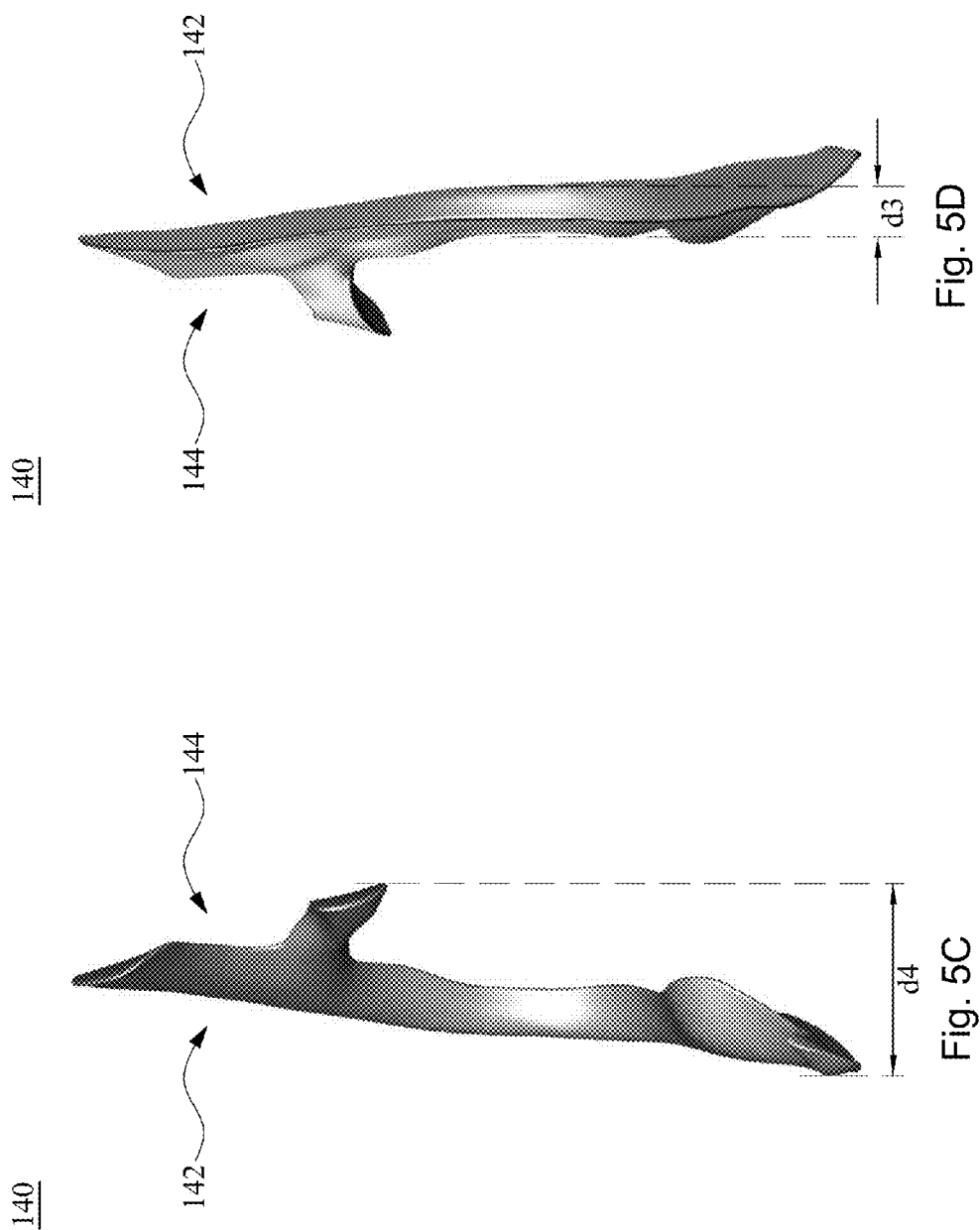

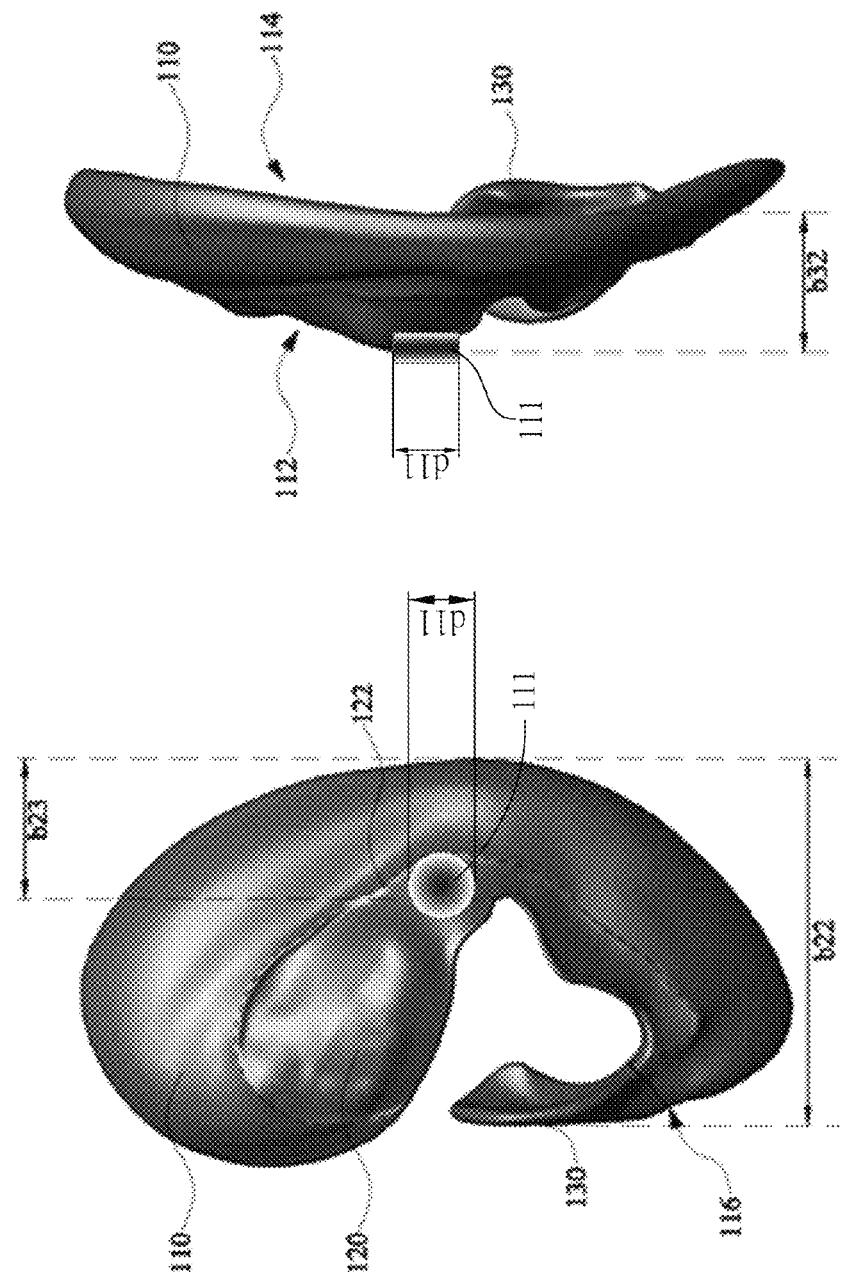

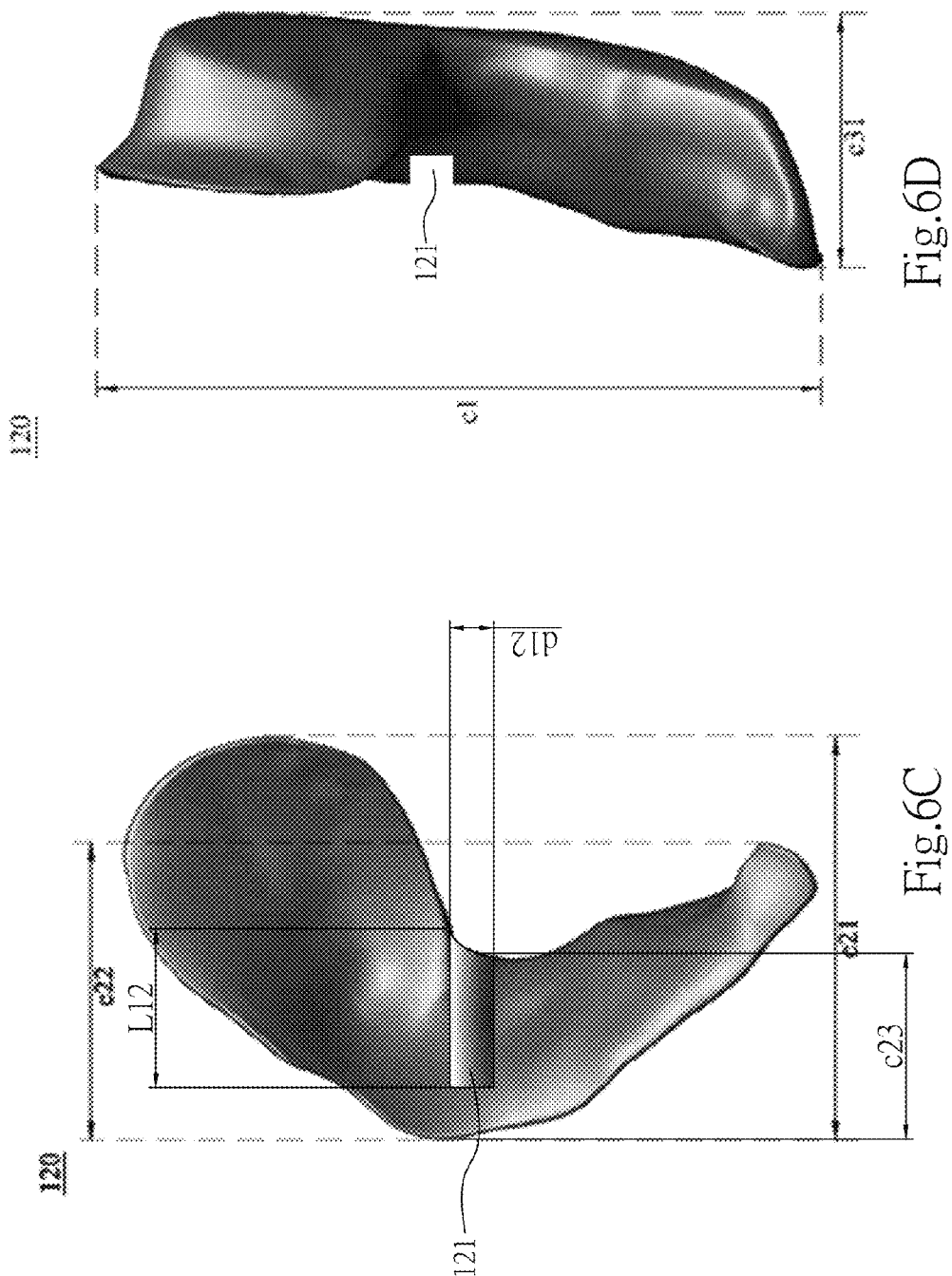

AURICULAR IMPLANT

RELATED APPLICATION

This application is a continuation-in-part (CIP) of U.S. Patent application for "AURICULAR IMPLANT", U.S. application Ser. No. 14/154,157 filed Jan. 13, 2014, and the subject matter of which is incorporated herein by reference.

This application claims priority to Taiwan Application Serial Number 102119987, filed Jun. 5, 2013, which is herein incorporated by reference.

BACKGROUND

Field of Invention

The present invention relates to an implant. More particularly, the present invention relates to an auricular implant.

Description of Related Art

According to the statistics, the incidence rate of the microtia is 1/5000-1/6000 in Asia and 1/7000 in the world. The incidence rate of the unilateral (one side only) microtia is 6 times of that of the bilateral (both sides) microtia; and there are twice as many right-sided microtias than left-sided microtias. For the unilateral microtia patient, it is desirable to reconstruct a prosthetic ear having similar shape with the normal ear. However, the sizes, the shapes and the outlines of the ears of patients are different, so the commercial available prosthetic ears having only few sizes, shapes and outlines cannot fit the normal ears of different patients well. Hence, it is desirable to provide a flexible and adjustable implant, which can fit the normal ears of different patients well.

In addition, the microtia occurs when the auricle is formed in the embryonic period. Approximately from the third week of the embryogenesis, the embryonic cell in the ectoderm has pathological changes, resulting in arrested development of external ear, which is referred to as the microtia in clinical. The clinical symptom of the microtia is mainly the defect of the auricular appearance in addition to the hearing abnormity. Thus, the microtia patient usually requires an auricular reconstruction. Besides, for the patient who has a severe trauma on his/her head, the auricular reconstruction is also necessary.

Currently, there are three common ways of the auricular reconstruction. The first way is wearing an ear model; the second way is using a medpor; and the third way is using an autogenous cartilage graft for reconstruction. The auricular reconstruction with autogenous cartilage is the top choice in the clinical. However, a two-stage surgery is required for the autogenous costal cartilage reconstruction. In the first stage in which the auricular model is plane rather than stereo, the patient's costal cartilage is taken out, carved into the shape of the ear bone, and then implanted subcutaneously. The second stage of the surgery is performed about six months later after the first stage. The surgeon raises the ear flap and implants the above auricular model, and then the auricular model is formed as a stereo ear. It is very difficult to employ this method. Besides, this method is suitable for the auricular reconstruction only when the patient's thorax is developed to above 60 cm or when the patients are over ten years old. Furthermore, the region where the costal cartilage is taken out will cause severe pain for 3 to 4 days after the surgery and also leave a scar. The living quality of the patient will be seriously affected in one month after the surgery.

In recent years, due to the improvement of medical materials, people place high hopes on the artificial materials, which may be the second best choice compared to the autogenous cartilage. Moreover, owing to the convenience of artificial materials in the clinic without complex carving techniques, some surgeons have already used the first way and the second way of reconstruction. In the first way, an externally hang-type prosthetic ear is used, wherein silicone is used to form the ear model, and a bone nail is implanted at the corresponding position of the ear to hang the silicone ear model; however, the externally hang-type prosthetic ear needs to be replaced every 2 to 5 years, and the bone nail requires a life-long maintenance to prevent the bone nail from piercing the skin. Thus, the first way is not the top choice.

In the second way, a Medpor® implant is used, but its flexibility is not good enough and it is easily broken after the reconstruction surgery. Referring to U.S. Pat. No. 5,433,748, an auricular implant is described. The material of the auricular implant is an elastic and porous polyethylene, which forms a structure including an auricular framework and a spiral skeleton. However, this auricular implant is a plane model such that it cannot be supported during the reconstructive surgery process, and after the surgery, it may not look like the naturally developed auricle in appearance very much. Furthermore, since the material of this auricular implant is thermoplastic polyethylene, it is necessary to provide certain temperature to change the auricular appearance. Besides, the material is hard and the plasticity and elasticity is finite. As a result, patient's skin may be wounded or the implant may be exposed due to collision, extrusion or thinning of ear skin caused by the implant, resulting in deformation of the auricular appearance.

Thus, the main task in the industry is how to prepare the auricular implant that looks more like the naturally developed auricle from the artificial material.

SUMMARY

In view of the problems in the prior art, an auricular implant is disclosed in the present invention, which can provide the integrity of the auricular appearance and looks more like the naturally developed auricle in appearance after the reconstructive surgery.

According to one aspect of the present invention, an auricular implant is provided, including an auricular base and a supporting member. The auricular base has a first side and a second side opposite to the first side, wherein the first side thereof is disposed with a position unit. The supporting member having a thickness and a recess, wherein the position unit of the auricular base is disposed in the recess of the supporting member to adhere the supporting member to the first side of the auricular base for forming a stereoscopic disk-like structure.

According to an embodiment of the present invention, the dimension scale of the maximum length:maximum width:maximum thickness of the auricular base is in the range of 45-80:28-45:8-22.

According to another embodiment of the present invention, the auricular base has a head, a middle recess and a tail that are located adjacent to each other, and the tail has a connection end. The auricular base further includes a connector connected to the connection end of the auricular base, extending from the connection end towards the middle recess.

According to a further embodiment of the present invention, the auricular base has a maximum length between the head and the tail along the length direction, a first width between a outer side of the middle recess and the head along the width direction, a second width between the outer side of the middle recess and the connector along the width direction and a third width between an inner side and the outer side of the middle recess along the width direction. The dimension scale of the maximum length:the first width:the second width:the third width of the auricular base is in the range of 45-80:28-45:25-40:9-15. The auricular base has a maximum thickness between both ends of the second side and the first side, and a minimum thickness between the middle recess of the second side and the first side. The dimension scale of the maximum thickness:minimum thickness of the auricular base is in the range of 13-22: 8-13.

According to an embodiment of the present invention, the dimension scale of length:width:thickness of the supporting member is in the range of 30-50: 18-30:7-18.

According to another embodiment of the present invention, the supporting member has an elongated structure, including a head, a middle portion and a tail connected to each other. The supporting member has a maximum length between the head and the tail along the length direction, a first width between the head and the outer side of the middle portion along the width direction, a second width between the tail and the middle portion and a third width between an inner side and the outer side of the middle portion. The dimension scale of the maximum length:the first width:the second width:the third width is in the range of 30-50:18-30:14-22:8-14. The supporting member has a maximum thickness and a minimum thickness, and the dimension scale of the maximum thickness:minimum thickness is in the range of 11-18:7-12.

According to an embodiment of the present invention, the structure of the auricular implant further includes a spiral member having a raised surface and a plane surface opposite to the raised surface. The spiral member is adhered to the second side of the auricular base in the plane surface, and completely held in an area of the second side of the auricular base.

According to an embodiment of the present invention, the spiral member has a Y-shaped bending structure. The spiral member has a maximum length along the length direction, a maximum width along the width direction, and a thickness in the middle portion of the spiral member. The dimension scale of the maximum length:maximum width:thickness of the spiral member is in the range of 35-55:20-35:2-4.

According to an embodiment of the present invention, the dimension scale of length:width:thickness of the auricular implant is in the range of 45-80:28-45:13-26.

According to another embodiment of the present invention, the auricular implant is a center model formed of a solid or non-porous material, having a layer of porous material coated on the outer side of the center model.

According to a further embodiment of the present invention, the solid or non-porous material is silicone (polydimethylsiloxane), polyurethane or fluoroelastomer. A layer of polytetrafluoroethylene is coated on the outer side of the center model.

According to a further embodiment of the present invention, the shape of the position unit on the auricular base is not particularly limited. For example, the position unit can be in a circular shape, a rectangular shape or other shapes. Preferably, the position unit is a circular position unit. In addition, the size of the position unit is also not particularly limited, as long as the purpose of fixing a relative position between the auricular base and the supporting member can be achieved.

According to a further embodiment of the present invention, the shape of the recess of the supporting member is not particularly limited, as long as the position unit of the auricular base can be positioned therein. For example, when the position unit is a circular position unit, a width of the recess of the supporting member is substantially identical to a diameter of the circular position unit. Preferably, the recess is a stripe recess, and the location of the position unit in the recess can be adjusted according to the desired shapes of the auricular implant. The recess and the position unit can facilitate the user to assemble the supporting member and the auricular base easily, quickly and precisely.

In the aforementioned embodiments of the present invention, when the auricular implant comprises two pieces of the auricular base and the supporting member, these two pieces can be assembled by any means known in the art, such as a binder, a suture, or a combination thereof. Preferably, the auricular base and the supporting member are assembled via a suture.

In the aforementioned embodiments of the present invention, when the auricular implant comprises three pieces of the auricular base, the supporting member and the spiral member, these three pieces can also be assembled by any means know in the art, such as a binder, a suture, or a combination thereof. Preferably, the auricular base and the supporting member is assembled via a suture.

However, the means for assembling these pieces (either two pieces or three pieces) of the present invention is not particularly limited to the aforementioned means, as long as the related position between these pieces are confirmed in advance, and any means known in the art can be used to fix these pieces.

BRIEF DESCRIPTION OF THE DRAWINGS

In order to make the above and other aspects, features, advantages, and embodiments of the present invention more apparent, the accompanying drawings are described as follows:

FIG. 1A is a front view of an auricular implant according to an embodiment of the present invention;

FIG. 1B is a rear view of the auricular implant according to an embodiment of the present invention;

FIG. 1C is a right side view of the auricular implant according to an embodiment of the present invention;

FIG. 1D is a left side view of the auricular implant according to an embodiment of the present invention;

FIG. 2A is a front view of a auricular base in the auricular implant according to another embodiment of the present invention;

FIG. 2B is a rear view of the auricular base in the auricular implant according to another embodiment of the present invention;

FIG. 4A is a front view of an auricular implant according to another embodiment of the present invention;

FIG. 4B is a rear view of the auricular implant according to another embodiment of the present invention;

FIG. 5A is a front view of a spiral member in the auricular implant according to an embodiment of the present invention;

FIG. 5B is a rear view of the spiral member in the auricular implant according to an embodiment of the present invention;

FIG. 5C is a right side view of the spiral member in the auricular implant according to an embodiment of the present invention;

FIG. 5D is a left side view of the spiral member in the auricular implant according to an embodiment of the present invention;

FIG. 6A is a rear view of the auricular base in the auricular implant according to further another embodiment of the present invention;

FIG. 6B is a left side view of the auricular base in the auricular implant according to further another embodiment of the present invention;

FIG. 6C is a rear view of the supporting member in the auricular implant according to further another embodiment of the present invention; and FIG. 6D is another view of the supporting member from a right side of FIG. 6C according to further another embodiment of the present invention.

DETAILED DESCRIPTION

Figure 2D:
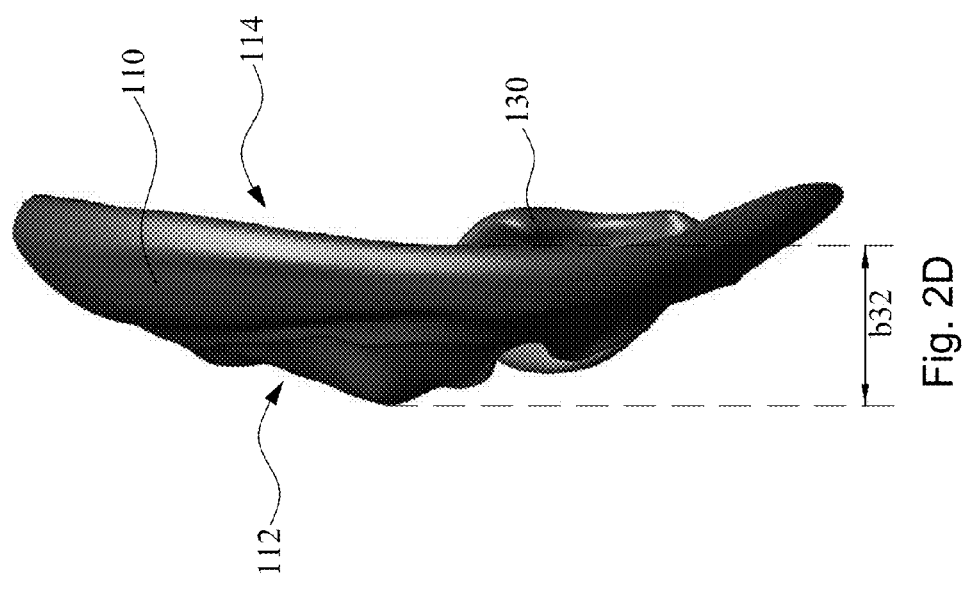
FIG. 2D is a left side view of the auricular base in the auricular implant according to another embodiment of the present invention.

In order to make the description of the present invention more detailed and more comprehensive, various aspects and specific embodiments of the present invention are described below illustratively. However, these illustrated aspects and specific embodiments are not the only way for implementing or using the present invention. In cases that are beneficial, the embodiments disclosed hereinafter may be combined with or replaced by each other, or alternatively other embodiments may be appended to an embodiment without any further statement or illustration.

Referring to FIGS. 1A-1D, a front view, a rear view, a right side view and a left side view of an auricular implant 100 are respectively illustrated according to an embodiment of the present invention. A structure of the auricular implant 100 includes an auricular base 110 and a supporting member 120. As shown in FIG. 1C, the auricular base 110 has a first side 112 and a second side 114 opposite to the first side 112. The supporting member 120 having a thickness is matchingly adhered to the first side 112 for forming a stereoscopic disk-like structure.

As shown in FIG. 1A, when viewed from the front, the auricular implant 100 has a maximum length a1 and a maximum width a2. As shown in FIG. 1C, when viewed from the side, the auricular implant 100 has a maximum thickness a31. In an embodiment, the dimension scale of the maximum length a1:maximum width a2:maximum thickness a31 of the auricular implant 100 is in the range of 45-80:28-45:13-26. In another embodiment, when viewed from the side, the auricular implant 100 has a first thickness a32 between a middle recess in the second side 114 of the auricular base 110 and an outer side of the supporting member 120 (with reference to FIG. 1D). The dimension scale of the maximum length a1:maximum width a2:maximum thickness a31:the first thickness a32 of the auricular implant 100 is in the range of 45-80:28-45:13-26:9-14.

Referring to FIGS. 2A-2D, a front view, a rear view, a right side view and a left side view of the auricular base 110 in the auricular implant 100 are respectively illustrated according to an embodiment of the present invention. As shown in FIG. 2A, the auricular base 110 has a head 110a, a middle recess 110b and a tail 110c which are located adjacent to each other, and the tail 110c has a connection end 116, which can also be seen with reference to FIG. 1A. In an embodiment, the auricular base 110 further includes a connector 130 connected to the connection end 116, which extends from the connection end 116 towards the middle recess 110b. As shown in FIG. 2B, when viewed from the rear, the auricular base 110 has an outline 122 depicted along the periphery of the middle recess 110b. When the auricular base 110 is matchingly adhered to the supporting member 120, the outline 122 is used to facilitate aligning with the desired binding position of the supporting member 120. In an embodiment, referring to FIGS. 2A and 2C, the dimension scale of the maximum length b1:maximum width b21:maximum thickness b31 of the auricular base 110 is in the range of 45-80:28-45:8-22.

As shown in FIG. 2A, when viewed from the front, the auricular base 110 has a maximum length b1 between the head 110a and the tail 110c along the length direction, a first width b21 (the maximum width described above) between the outer side of the middle recess 110b and the head 110a along the width direction, a second width b22 (with reference to FIG. 2B) between the outer side of the middle recess 110b and the connector 130 and a third width b23 (with reference to FIG. 2B) between the inner side and the outer side of the middle recess 110b. In another embodiment, the dimension scale of the maximum length b1:the first width b21:the second width b22:the third width b23 of the auricular base 110 is in the range of 45-80:28-45:25-40:9-15.

Figure 2C:
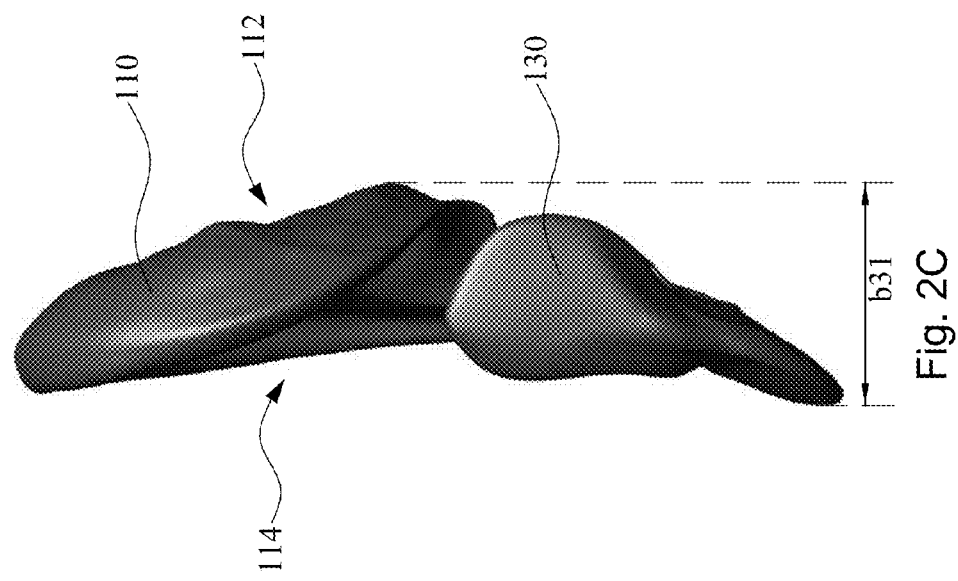
FIG. 2C is a right side view of the auricular base in the auricular implant according to another embodiment of the present invention.

As shown in FIG. 2C, when viewed from the side, the auricular base 110 has a maximum thickness b31 between both ends of the second side 114 and the first side 112. As shown in FIG. 2D, the auricular base 110 has a minimum thickness b32 between the middle recess 110b of the second side 114 and the first side 112. In a further embodiment, the dimension scale of the maximum thickness b31:minimum thickness b32 of the auricular base is in the range of 13-22:8-13.

Referring to FIGS. 3A-3D, a front view, a rear view, a right side view and a left side view of the supporting member 120 in the auricular implant 100 are respectively illustrated according to an embodiment of the present invention. In an embodiment, referring to FIGS. 3A-3D, the dimension scale of the maximum length c1:maximum width c21:maximum thickness c31 of the supporting member 120 is in the range of 30-50:18-30:7-18.

Figure 3B:
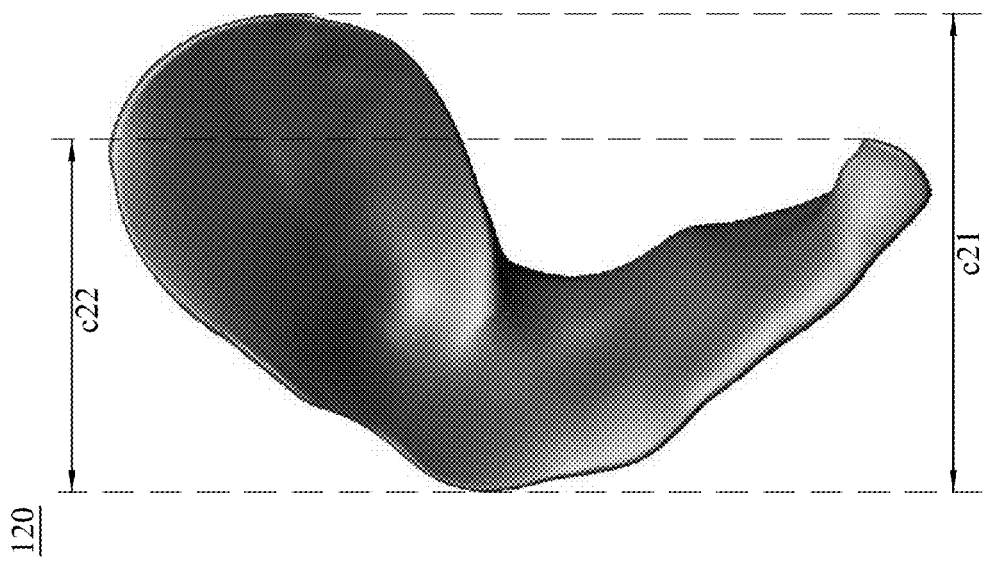
FIG. 3B is a rear view of the supporting member in the auricular implant according to an embodiment of the present invention.
Figure 3A:
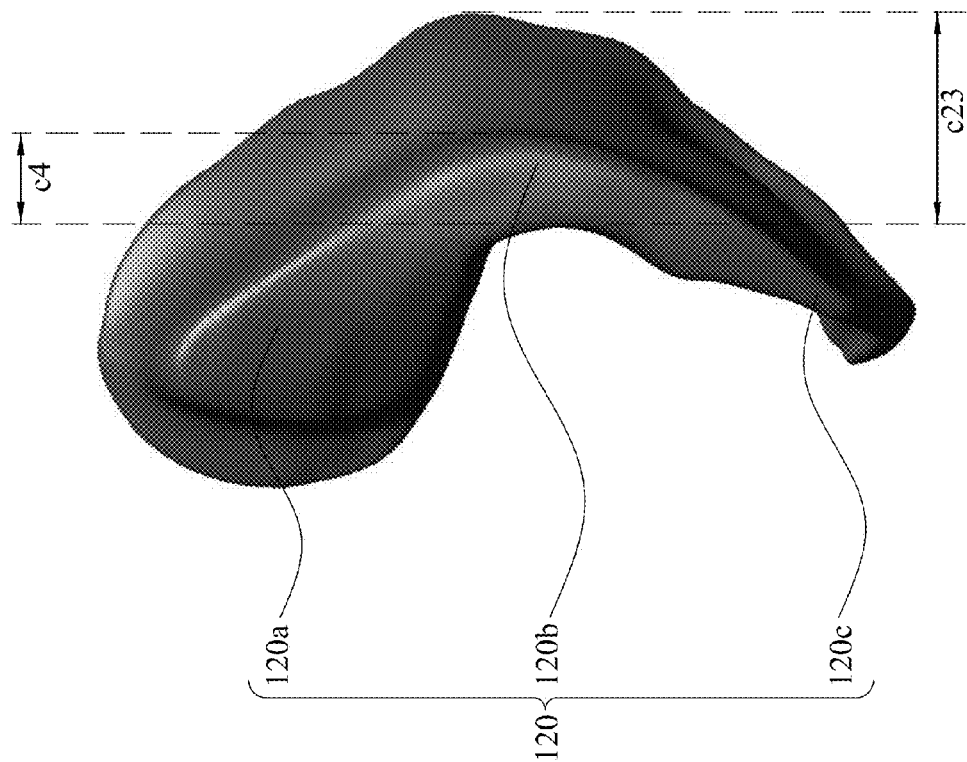
FIG. 3A is a front view of a supporting member in the auricular implant according to an embodiment of the present invention.

As shown in FIG. 3A, the supporting member 120 has an elongated structure, including a head 120a, a middle portion 120b and a tail 120c connected to each other. When viewed from the front, the supporting member 120 has a maximum length c1 (with reference to FIG. 3C) between the head 120a and the tail 120c along the length direction, a first width (the maximum width) c21 (with reference to FIG. 3B) between the head 120a and the outer side of the middle portion 120b along the width direction, a second width c22 (with reference to FIG. 3B) between the tail 120c and the middle portion 120b and a third width c23 (with reference to FIG. 3A) between the inner side and the outer side of the middle portion 120b. In another embodiment, the dimension scale of the maximum length c1:the first width c21:the second width c22:the third width c23 is in the range of 30-50:18-30:14-22:8-14.

Figure 3C:
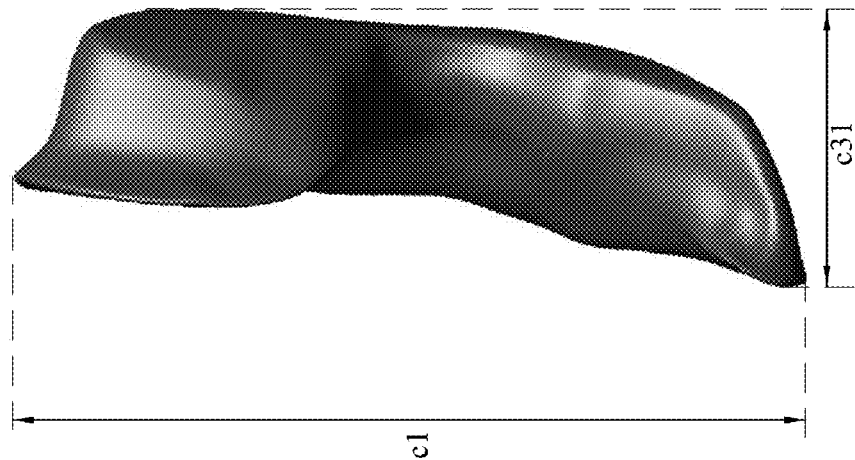
FIG. 3C is a right side view of the supporting member in the auricular implant according to an embodiment of the present invention.
Figure 3D:
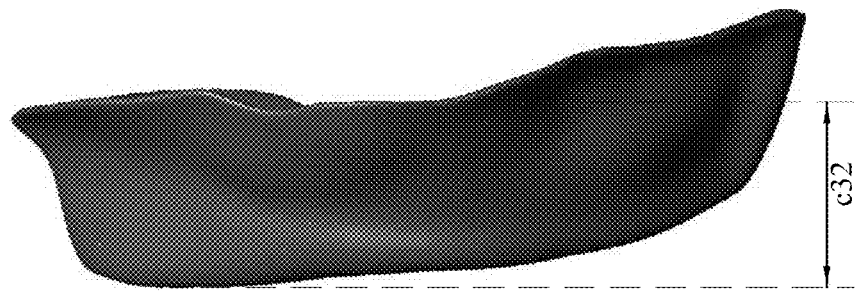
FIG. 3D is a left side view of the supporting member in the auricular implant according to an embodiment of the present invention.

As shown in FIG. 3C and FIG. 3D, when viewed from the side, the supporting member 120 has a maximum thickness c31 and a minimum thickness c32. In another embodiment, the dimension scale of the maximum thickness c31:minimum thickness c32 is in the range of 11-18:7-12.

Figure 4C:
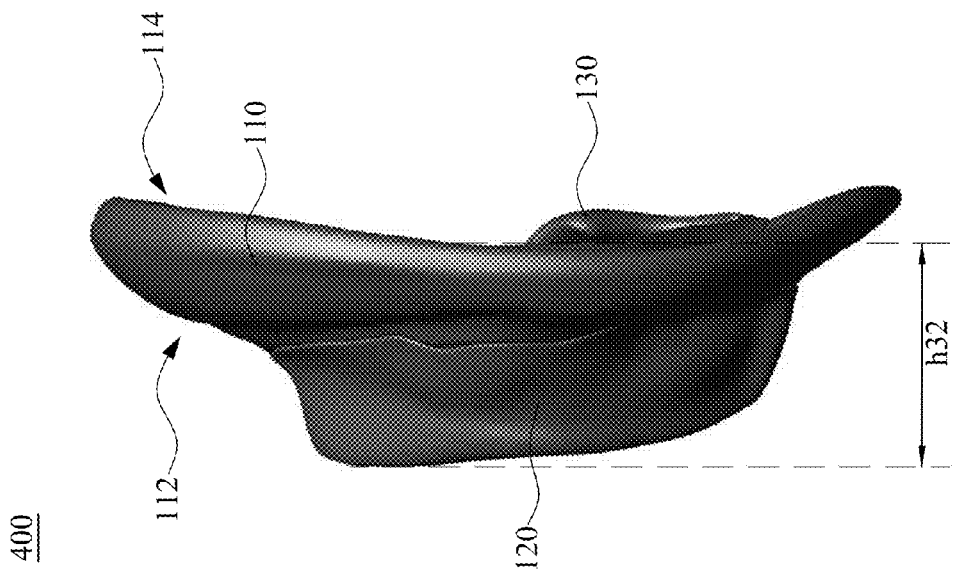
FIG. 4C is a right side view of the auricular implant according to another embodiment of the present invention.

Referring to FIGS. 4A-4F, a front view, a rear view, a right side view, a left side view, a top view and a bottom view of the auricular implant 400 are respectively illustrated according to another embodiment of the present invention. The structure of the auricular implant 400 further includes a spiral member 140 in addition to the auricular base 110, the supporting member 120 and the connector 130 as described above. As shown in FIG. 4A, the spiral member 140 has a raised surface 142 and a plane surface 144 opposite to the raised surface 142, and the spiral member 140 is adhered to the second side 114 of the auricular base 110 in the plane surface 144 with reference to FIG. 5C and FIG. 5D. In an embodiment, the spiral member 140 is completely held in an area of the second side 114 of the auricular base 110.

Figure 4D:
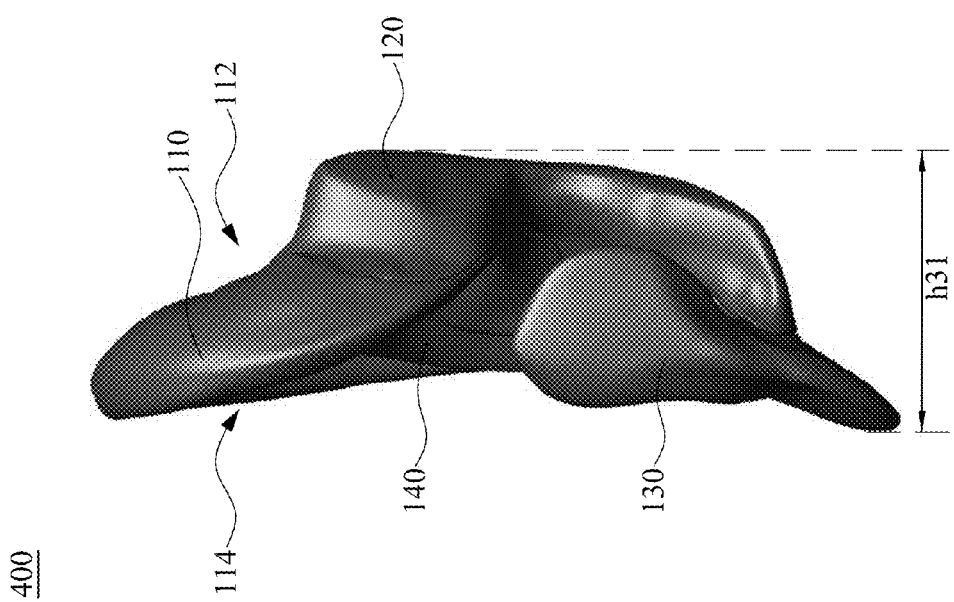
FIG. 4D is a left side view of the auricular implant according to another embodiment of the present invention.
Figure 4F:
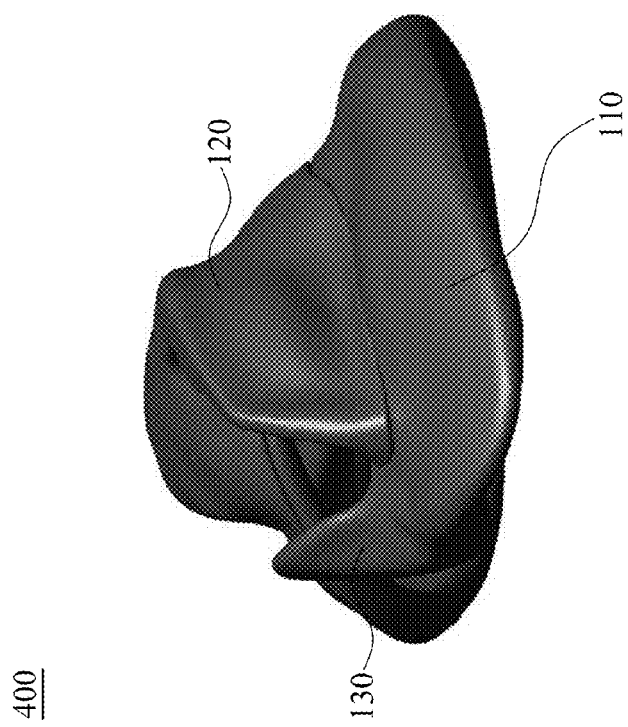
FIG. 4F is a bottom view of the auricular implant according to another embodiment of the present invention.
Figure 4E:
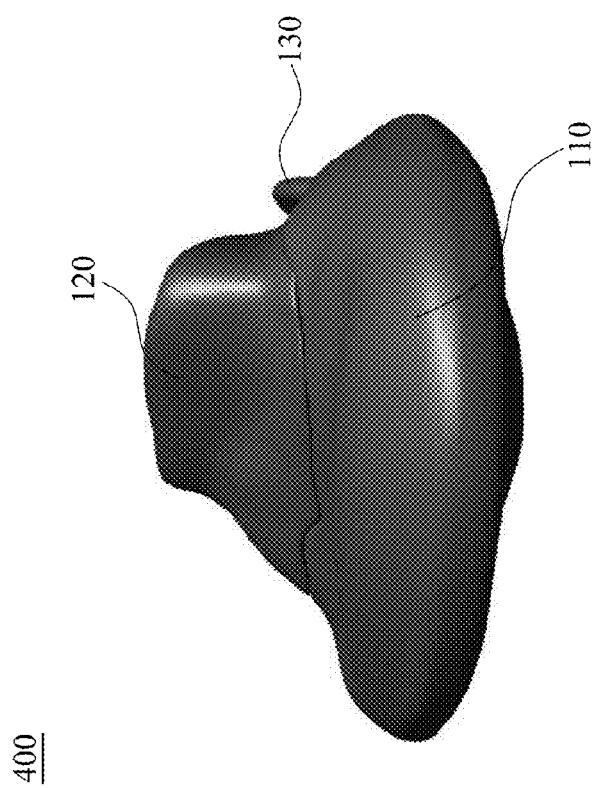
FIG. 4E is a top view of the auricular implant according to another embodiment of the present invention.

As shown in FIG. 4A, when viewed from the front, the auricular implant 400 has a maximum length h1, a maximum width h21, a width h22 between the connector 130 and the outer side of the auricular base 110 and a spacing h23 between the recess of the spiral member 140 and the connector 130. As shown in FIG. 4B, when viewed from the rear, the auricular implant 400 has a width h24 between the recess of the supporting member 120 and the outer side of the auricular base 110. As shown in FIGS. 4C-4D, when viewed from the side, the auricular implant 400 has a maximum thickness h31 and a minimum thickness h32.

Referring to FIGS. 5A-5D, a front view, a rear view, a right side view and a left side view of the spiral member 140 in the auricular implant 400 are respectively illustrated according to an embodiment of the present invention. As shown in FIG. 5A, the spiral member 140 has a Y-shaped bending structure. When viewed from the front or the rear, the spiral member 140 has a maximum length d1 along the length direction and a maximum width d2 along the width direction. When viewed from the left side, as shown in FIG. 5D, the spiral member 140 has a thickness d3 in the middle portion thereof. When viewed from the right side, as shown in FIG. 5C, the spiral member 140 has a maximum thickness d4. In an embodiment, the dimension scale of the maximum length d1:maximum width d2:thickness d3 of the spiral member 140 is in the range of 35-55:20-35:2-4.

Referring to FIGS. 6A-6B, a rear view and a left side view of the auricular base 110 are respectively illustrated according to further another embodiment of the present invention. Referring to FIG. 6C, a rear view of the supporting member 120 is illustrated according to further another embodiment of the present invention. The structure of the auricular implant of the present embodiment is similar to those illustrated before, except for the following differences.

As shown in FIGS. 6A and 6B, the first side 112 of the auricular base 110 is disposed with a position unit 111, which is a circular position unit and has a diameter d11. Herein, a circular position unit is illustrated in FIGS. 6A and 6B; however, in other embodiment of the present invention, the shape the position unit 111 is not limited to that illustrated in FIGS. 6A and 6B.

In addition, as shown in FIG. 6D, the supporting member 120 has a recess 121. As shown in FIGS. 6A-6D, when the supporting member 120 is assembled to the auricular base 110, the position unit 111 corresponds to and is disposed in the recess 121 to matchingly adhere the supporting member 120 to the first side 112 of the auricular base 110. Herein, the recess 121 of the present embodiment is a stripe recess, which has a width d12 and a length L12. In the present embodiment, the width d12 is substantially identical to the diameter d11 of the position unit 111, so the position unit 111 can be located therein well. In addition, the length L12 of the recess 121 is not particularly limited, and it can be shorter than or identical to the width c23. In the present embodiment, the length L12 is shorter than the width c23 and much larger than the diameter d11 of the position unit 111. In the case that the length L12 is larger than the diameter d11 of the position unit 111, the location of the position unit 111 in the recess 121 can be adjusted according to the desired shape of the auricular implant. However, in other embodiment of the present invention, the length L12 may be substantially identical to the diameter d11 of the position unit 111.

Furthermore, as shown in FIGS. 6A-6D, the recess 121 of the present embodiment is a lateral stripe recess; hence, when the position unit 111 corresponds to and is disposed in the recess 121, the position unit 111 can be moved laterally. In addition, the position unit 111 is a circular position unit; hence, the position unit 111 can also be rotated in the recess 121. By laterally moving and rotating the position unit 111, the position unit 111 can be positioned at a predetermined position in the recess 121.

In the aforementioned embodiments of the present invention, when the auricular implant is consisted of two pieces including the auricular base 110 and the supporting member 120, or three pieces further including the spiral member 140, these pieces can be fixed with each other via a binder, a suture, or a combination thereof. Preferably, these pieces are fixed with each other via the suture or via both the suture and the binder. During the process for assembling these pieces with the suture, the doctor may slightly adjust the angles between each pieces and/or bending levels of these pieces, to accomplish the purpose of forming auricular implants with different shapes. When the binder is also used, these pieces can be assembled with the binder in advance, and then fixed via the suture.

The center model of the auricular implant is formed of a solid or non-porous material such as silicone (polydimethylsiloxane), polyurethane or fluoroelastomer, and a layer of porous material such as polytetrafluoroethylene is coated on the outer side of the center model. In an embodiment, preferably, the material of the center model in the aforesaid auricular implant is silicone. That is, the silicone is shaped into the required auricular implant, and a layer of expandable polytetrafluoroethylene (ePTFE) is coated on the outer side of the auricular implant. When the auricular implant is formed of a non-porous material, the angles between the auricular base 110 and the supporting member 120 (and the spiral member 140) and/or bending levels thereof can easily be adjusted, to accomplish the purpose of forming auricular implants with different shapes.

The silicone with higher density is suitable for preparing an implant model. However, its defect is not biocompatible, tending to cause a tissue fibrosis, thereby leading to a tissue contracture, and thus it is not appropriate to contact the organism directly. Thus, a layer of porous, softer and highly biocompatible polytetrafluoroethylene is coated on the outer side of the center model. Its property of high biocompatibility can not only prevent the tissue contracture but also extend the time of the implant maintained in the organism. Its porous property can enable the surrounding soft tissues to grow inward, which is helpful to fix the implant. Besides, its material is softer such that when the organism is actuated, the auricular implant is not liable to be deformed due to collision. By the way, the polytetrafluoroethylene costs too much and its material is so soft that it is easy to be deformed. Furthermore, since it is a porous material, it will cause a collapse after long-term use. Thus, the polytetrafluoroethylene is not suitable to be used as the material of the whole auricular implant.

The auricular implant of the present invention can be used in the auricular reconstruction for the organism. According to the foregoing description, the composition of the auricular implant at least includes the auricular base and the supporting member, and may further include the connector and/or the spiral member. In the clinical application, the auricular implant is prepared depending upon requirements of users.

EMBODIMENT

The following embodiments are used for illustrating specific aspects of the present invention in details, so that those of ordinary skills in the art of the present invention can implement the present invention accordingly. The following embodiments are not intended to limit the present invention.

Auricular Implant

Embodiments A1-A26

Embodiments A1-A26 are the embodiments of the auricular implant of the present invention. The auricular implant of each embodiment includes an auricular base, a supporting member, a spiral member and a connector. In each embodiment, the followings are measured: the maximum length h1, the maximum width h21, the width h22 between the connector and the outer side of the auricular base and the spacing h23 between the recess of the spiral member and the connector when the implant is viewed from the front, the width h24 between the recess of the supporting member and the outer side of the auricular base when the implant is viewed from the rear, the maximum thickness h31 and the minimum length h32 of the implant when the implant is viewed from the side, with reference to FIGS. 4A-4D. The measurement results are shown in Table 1 as follows.

TABLE 1

(unit: mm)

| Embodiment | h1 | h21 | h22 | h23 | h24 | h31 | h32 |
|---|---|---|---|---|---|---|---|
| A1 | 50.0 | 28.7 | 25.8 | 15.0 | 15.2 | 16.5 | 13.4 |
| A2 | 51.0 | 29.2 | 26.3 | 15.3 | 15.5 | 16.8 | 13.7 |
| A3 | 52.0 | 29.8 | 26.8 | 15.6 | 15.8 | 17.2 | 14.0 |
| A4 | 53.0 | 30.4 | 27.3 | 15.9 | 16.1 | 17.5 | 14.2 |
| A5 | 54.0 | 31.0 | 27.8 | 16.2 | 16.4 | 17.8 | 14.5 |
| A6 | 55.0 | 31.5 | 28.3 | 16.5 | 16.7 | 18.2 | 14.8 |
| A7 | 56.0 | 32.1 | 28.8 | 16.8 | 17.0 | 18.5 | 15.0 |
| A8 | 57.0 | 32.7 | 29.4 | 17.1 | 17.3 | 18.8 | 15.3 |
| A9 | 58.0 | 33.3 | 29.9 | 17.4 | 17.6 | 19.1 | 15.6 |
| A10 | 59.0 | 33.8 | 30.4 | 17.7 | 17.9 | 19.5 | 15.8 |
| A11 | 60.0 | 34.4 | 30.9 | 18.0 | 18.2 | 19.8 | 16.1 |
| A12 | 61.0 | 35.0 | 31.4 | 18.3 | 18.5 | 20.1 | 16.4 |
| A13 | 62.0 | 35.5 | 31.9 | 18.6 | 18.8 | 20.5 | 16.6 |
| A14 | 63.0 | 36.1 | 32.4 | 18.9 | 19.1 | 20.8 | 16.9 |
| A15 | 64.0 | 36.7 | 33.0 | 19.2 | 19.4 | 21.1 | 17.2 |
| A16 | 65.0 | 37.3 | 33.5 | 19.5 | 19.7 | 21.5 | 17.4 |
| A17 | 66.0 | 37.8 | 34.0 | 19.8 | 20.0 | 21.8 | 17.7 |
| A18 | 67.0 | 38.4 | 34.5 | 20.1 | 20.3 | 22.1 | 18.0 |
| A19 | 68.0 | 39.0 | 35.0 | 20.4 | 20.6 | 22.4 | 18.2 |
| A20 | 69.0 | 39.6 | 35.5 | 20.7 | 20.9 | 22.8 | 18.5 |
| A21 | 70.0 | 40.1 | 36.1 | 21.0 | 21.2 | 23.1 | 18.8 |
| A22 | 71.0 | 40.7 | 36.6 | 21.3 | 21.5 | 23.4 | 19.1 |
| A23 | 72.0 | 41.3 | 37.1 | 21.6 | 21.8 | 23.8 | 19.3 |
| A24 | 73.0 | 41.9 | 37.6 | 21.9 | 22.1 | 24.1 | 19.6 |
| A25 | 74.0 | 42.4 | 38.1 | 22.2 | 22.4 | 24.4 | 19.9 |
| A26 | 75.0 | 43.0 | 38.6 | 22.5 | 22.8 | 24.8 | 20.1 |

According to the aforesaid Table 1, the auricular implant with the h1 dimension of 58 mm is more commonly used for Asians, and the auricular implant with the h1 dimension of 60 mm is more commonly used for Westerners.

In addition, the dimensions of each composition of the auricular implant in Embodiments A1-A26 are listed as well. The dimensions of the auricular base (including the connector) are listed in Table 2. The dimensions of the supporting member are listed in Table 3 and the dimensions of the spiral member are listed in Table 4.

The followings are measured: the maximum length b1 and the maximum width b21 of the auricular base, the width b22 between the connector and the outermost side of the middle recess and the width b23 between the outer side and the inner side of the middle recess, the maximum thickness b31 and the minimum thickness b32 viewed from the side, and the spacing b4 between the outermost side of the outline in the middle recess and the connector, with reference to FIGS. 2A-2D. The measurement results are shown in Table 2 as follows.

TABLE 2

(unit: mm)

| Embodiment | b1 | b21 | b22 | b23 | b31 | b32 | b4 |
|---|---|---|---|---|---|---|---|
| A1 | 50.0 | 28.7 | 25.8 | 9.9 | 13.4 | 9.1 | 15.3 |
| A2 | 51.0 | 29.3 | 26.3 | 10.1 | 13.6 | 9.3 | 15.6 |
| A3 | 52.0 | 29.8 | 26.8 | 10.3 | 13.9 | 9.4 | 15.9 |
| A4 | 53.0 | 30.4 | 27.3 | 10.5 | 14.2 | 9.6 | 16.2 |
| A5 | 54.0 | 31.0 | 27.8 | 10.7 | 14.4 | 9.8 | 16.6 |
| A6 | 55.0 | 31.6 | 28.4 | 10.9 | 14.7 | 10.0 | 16.9 |
| A7 | 56.0 | 32.1 | 28.9 | 11.1 | 15.0 | 10.2 | 17.2 |
| A8 | 57.0 | 32.7 | 29.4 | 11.3 | 15.2 | 10.4 | 17.5 |
| A9 | 58.0 | 33.3 | 29.9 | 11.5 | 15.5 | 10.5 | 17.8 |
| A10 | 59.0 | 33.9 | 30.4 | 11.7 | 15.8 | 10.7 | 18.1 |
| A11 | 60.0 | 34.4 | 30.9 | 11.9 | 16.0 | 10.9 | 18.4 |
| A12 | 61.0 | 35.0 | 31.4 | 12.1 | 16.3 | 11.1 | 18.7 |
| A13 | 62.0 | 35.6 | 32.0 | 12.3 | 16.6 | 11.3 | 19.0 |
| A14 | 63.0 | 36.1 | 32.5 | 12.5 | 16.8 | 11.4 | 19.3 |
| A15 | 64.0 | 36.7 | 33.0 | 12.7 | 17.1 | 11.6 | 19.6 |
| A16 | 65.0 | 37.3 | 33.5 | 12.8 | 17.4 | 11.8 | 19.9 |
| A17 | 66.0 | 37.9 | 34.0 | 13.0 | 17.6 | 12.0 | 20.2 |
| A18 | 67.0 | 38.4 | 34.5 | 13.2 | 17.9 | 12.2 | 20.5 |
| A19 | 68.0 | 39.0 | 35.1 | 13.4 | 18.2 | 12.3 | 20.8 |
| A20 | 69.0 | 39.6 | 35.6 | 13.6 | 18.4 | 12.5 | 21.2 |
| A21 | 70.0 | 40.2 | 36.1 | 13.8 | 18.7 | 12.7 | 21.5 |

TABLE 2-continued

| Embodiment | b1 | b21 | b22 | b23 | b31 | b32 | b4 (unit: mm) |
|---|---|---|---|---|---|---|---|
| A22 | 71.0 | 40.7 | 36.6 | 14.0 | 19.0 | 12.9 | 21.8 |
| A23 | 72.0 | 41.3 | 37.1 | 14.2 | 19.2 | 13.1 | 22.1 |
| A24 | 73.0 | 41.9 | 37.6 | 14.4 | 19.5 | 13.3 | 22.4 |
| A25 | 74.0 | 42.5 | 38.1 | 14.6 | 19.8 | 13.4 | 22.7 |
| A26 | 75.0 | 43.0 | 38.7 | 14.8 | 20.0 | 13.6 | 23.0 |

The followings are measured: the maximum length $c_1$ and the maximum width $c_{21}$ of the supporting member, the width $c_{22}$ between the tail and the outermost side of the middle recess and the width $c_{23}$ between the outer side and the inner side of the middle recess, the maximum thickness $c_{31}$, the minimum thickness $c_{32}$ and the width $c_4$ of the protuberance in the middle recess, with reference to FIGS. 3A-3D. The measurement results are shown in Table 3 as follows.

TABLE 3

| Embodiment | c1 | c21 | c22 | c23 | c31 | c32 | c4 (unit: mm) |
|---|---|---|---|---|---|---|---|
| A1 | 32.4 | 18.9 | 14.1 | 8.6 | 11.3 | 7.6 | 3.7 |
| A2 | 33.1 | 19.3 | 14.4 | 8.8 | 11.6 | 7.8 | 3.8 |
| A3 | 33.7 | 19.7 | 14.7 | 8.9 | 11.8 | 7.9 | 3.9 |
| A4 | 34.4 | 20.1 | 14.9 | 9.1 | 12.0 | 8.1 | 4.0 |
| A5 | 35.0 | 20.5 | 15.2 | 9.3 | 12.2 | 8.2 | 4.0 |
| A6 | 35.7 | 20.8 | 15.5 | 9.4 | 12.5 | 8.4 | 4.1 |
| A7 | 36.3 | 21.2 | 15.8 | 9.6 | 12.7 | 8.5 | 4.2 |
| A8 | 37.0 | 21.6 | 16.1 | 9.8 | 12.9 | 8.7 | 4.2 |
| A9 | 37.6 | 22.0 | 16.4 | 10.0 | 13.2 | 8.8 | 4.3 |
| A10 | 38.3 | 22.3 | 16.6 | 10.1 | 13.4 | 9.0 | 4.4 |
| A11 | 38.9 | 22.7 | 16.9 | 10.3 | 13.6 | 9.1 | 4.5 |
| A12 | 39.6 | 23.1 | 17.2 | 10.5 | 13.8 | 9.3 | 4.5 |
| A13 | 40.2 | 23.5 | 17.5 | 10.6 | 14.1 | 9.4 | 4.6 |
| A14 | 40.9 | 23.9 | 17.8 | 10.8 | 14.3 | 9.6 | 4.7 |
| A15 | 41.5 | 24.2 | 18.0 | 11.0 | 14.5 | 9.7 | 4.8 |
| A16 | 42.2 | 24.6 | 18.3 | 11.2 | 14.7 | 9.9 | 4.8 |
| A17 | 42.8 | 25.0 | 18.6 | 11.3 | 15.0 | 10.0 | 4.9 |
| A18 | 43.5 | 25.4 | 18.9 | 11.5 | 15.2 | 10.2 | 5.0 |
| A19 | 44.1 | 25.8 | 19.2 | 11.7 | 15.4 | 10.3 | 5.1 |
| A20 | 44.8 | 26.1 | 19.5 | 11.8 | 15.7 | 10.5 | 5.1 |
| A21 | 45.4 | 26.5 | 19.7 | 12.0 | 15.9 | 10.6 | 5.2 |
| A22 | 46.1 | 26.9 | 20.0 | 12.2 | 16.1 | 10.8 | 5.3 |
| A23 | 46.7 | 27.3 | 20.3 | 12.4 | 16.3 | 11.0 | 5.4 |
| A24 | 47.4 | 27.7 | 20.6 | 12.5 | 16.6 | 11.1 | 5.4 |
| A25 | 48.0 | 28.0 | 20.9 | 12.7 | 16.8 | 11.3 | 5.5 |
| A26 | 48.7 | 28.4 | 21.1 | 12.9 | 17.0 | 11.4 | 5.6 |

The followings are measured: the maximum length $d_1$ and the maximum width $d_2$ of the spiral member, the thickness $d_3$ of the middle portion and the maximum thickness $d_4$ viewed from the side, with reference to FIGS. 5A-5D. The measurement results are shown in Table 4 as follows.

TABLE 4

| Embodiment | d1 | d2 | d3 | d4 (unit: mm) |
|---|---|---|---|---|
| A1 | 36.3 | 20.9 | 2.2 | 8.8 |
| A2 | 37.0 | 21.3 | 2.3 | 9.0 |
| A3 | 37.7 | 21.7 | 2.3 | 9.2 |
| A4 | 38.5 | 22.1 | 2.4 | 9.4 |
| A5 | 39.2 | 22.5 | 2.4 | 9.5 |
| A6 | 39.9 | 23.0 | 2.5 | 9.7 |
| A7 | 40.6 | 23.4 | 2.5 | 9.9 |
| A8 | 41.4 | 23.8 | 2.5 | 10.1 |
| A9 | 42.1 | 24.2 | 2.6 | 10.2 |
| A10 | 42.8 | 24.6 | 2.6 | 10.4 |
| A11 | 43.5 | 25.0 | 2.7 | 10.6 |
| A12 | 44.3 | 25.5 | 2.7 | 10.8 |
| A13 | 45.0 | 25.9 | 2.8 | 10.9 |
| A14 | 45.7 | 26.3 | 2.8 | 11.1 |
| A15 | 46.4 | 26.7 | 2.9 | 11.3 |
| A16 | 47.2 | 27.1 | 2.9 | 11.5 |
| A17 | 47.9 | 27.6 | 2.9 | 11.7 |
| A18 | 48.6 | 28.0 | 3.0 | 11.8 |
| A19 | 49.4 | 28.4 | 3.0 | 12.0 |
| A20 | 50.1 | 28.8 | 3.1 | 12.2 |
| A21 | 50.8 | 29.2 | 3.1 | 12.4 |
| A22 | 51.5 | 29.6 | 3.2 | 12.5 |
| A23 | 52.3 | 30.1 | 3.2 | 12.7 |
| A24 | 53.0 | 30.5 | 3.3 | 12.9 |
| A25 | 53.7 | 30.9 | 3.3 | 13.1 |
| A26 | 54.4 | 31.3 | 3.3 | 13.2 |

Herein, the present invention provides auricular bases (including the connector), supporting members and spiral members with different dimension. During the operation, a doctor can choose one of them to obtain an auricular implant with a predetermined shape. For example, one auricular implant formed by the auricular base (including the connector) shown in Embodiment A11 of Table 2, the supporting member shown in Embodiment A5 of Table 3, and the spiral member shown in Embodiment A23 of Table 4 assembled to each other, has different shape from, another auricular implant formed by the auricular base (including the connector) shown in Embodiment A5 of Table 2, the supporting member shown in Embodiment A10 of Table 3, and the spiral member shown in Embodiment A6 of Table 4 assembled to each other. Even though only 26 kinds of auricular bases (including the connector), 26 kinds of supporting members and 26 kinds of spiral members are provided in the present invention, auricular implants with various shapes can be obtained.

An implant for the auricular reconstruction is provided in the present invention. The implant with high industrial applicability can be used in the auricular reconstruction for the microtia patient, the facial hypoplasia or the ear trauma. Its technical characteristic is that in addition to having a basic auricular base, the implant further includes a supporting member connected to the side of the auricular implant near the organism. This supporting member is contributed to supporting the auricular implant in order to form an auricle elevation angle with the organism. The shape of the implant can be adjusted based on the actual demand and the angle can also be adjusted based on the facial form of the user, in order to make the implant look more like the naturally developed auricle.

More specifically, compared to the conventional integrated auricular implants, the angles and the bending levels the auricular implant provided by the present invention can be adjusted by choosing different pieces and assembling different pieces with suture. Hence, the shape, the angle and the bending level of the obtained auricular implant can be adjusted based on the actual demand and the facial form of the user; and therefore the outline of obtained auricular implant can be more consistent with the naturally developed auricle of the microtia, facial hypoplasia or ear trauma patient.

Although the present invention has been disclosed with reference to the above embodiments, these embodiments are not intended to limit the present invention. It will be apparent to those of skills in the art that various modifications and variations can be made without departing from the spirit and scope of the present invention. Therefore, the scope of the present invention shall be defined by the appended claims.

What is claimed is:

1. An auricular implant, comprising:
an auricular base, having a first side and a second side opposite to the first side, wherein the first side thereof is disposed with a position unit;
a supporting member having a thickness and a recess, wherein the position unit of the auricular base is disposed in the recess of the supporting member to matchingly adhere the supporting member to the first side of the auricular base for forming an elongated arcuate structure that decreases in overall thickness from an axial edge to a radial edge; and
a spiral member having a raised surface and a plane surface opposite to the raised surface, the spiral member being adhered to the second side of the auricular base on the plane surface, wherein the spiral member has a Y-shaped bending structure.

2. The auricular implant of claim 1, wherein the spiral member is completely held in an area of the second side of the auricular base.

3. The auricular implant of claim 1, wherein a dimension scale of maximum length:maximum width:maximum thickness of the auricular base is in the range of 45-80:28-45:8-22.

4. The auricular implant of claim 1, wherein the auricular base has a head, a middle recess and a tail that are located adjacent to each other, and the tail has a connection end.

5. The auricular implant of claim 4, further comprising a connector connected to the connection end of the auricular base, which extends from the connection end towards the middle recess.

6. The auricular implant of claim 5, wherein the auricular base has a maximum length between the head and the tail along a length direction, a first width between a outer side of the middle recess and the head along a width direction, a second width between the outer side of the middle recess and the connector and a third width between an inner side and the outer side of the middle recess, wherein the dimension scale of the maximum length:the first width:the second width:the third width of the auricular base is in the range of 45-80:28-45:25-40:9-15.

7. The auricular implant of claim 5, wherein the auricular base has a maximum thickness between both ends of the second side and the first side, and a minimum thickness between the middle recess of the second side and the first side, and the dimension scale of the maximum thickness: minimum thickness of the auricular base is in the range of 13-22:8-13.

8. The auricular implant of claim 1, wherein the spiral member has a maximum length along the length direction, a maximum width along the width direction, and a thickness in the middle portion of the spiral member, wherein the dimension scale of the maximum length:maximum width: thickness of the spiral member is in the range of 35-55:20-35:2-4.

9. The auricular implant of claim 1, wherein the dimension scale of the maximum length:maximum width:maximum thickness of the supporting member is in the range of 30-50:18-30:7-18.

10. The auricular implant of claim 1, wherein the supporting member has an elongated structure, comprising a head, a middle portion and a tail that are connected to each other.

11. The auricular implant of claim 10, wherein the supporting member has a maximum length between the head and the tail along the length direction, a first width between the head and an outer side of the middle portion along the width direction, a second width between the tail and the middle portion and a third width between an inner side and the outer side of the middle portion, wherein the dimension scale of the maximum length:the first width:the second width:the third width is in the range of 30-50:18-30:14-22:8-14.

12. The auricular implant of claim 10, wherein the supporting member has a maximum thickness and a minimum thickness, and the dimension scale of the maximum thickness:the minimum thickness is in the range of 11-18:7-12.

13. The auricular implant of claim 1, wherein the dimension scale of the length:width:thickness of the auricular implant is in the range of 45-80:28-45:13-26.

14. The auricular implant of claim 1, wherein the auricular implant is a center model formed of a solid or non-porous material, having a layer of porous material coated on an outer side of the center model.

15. The auricular implant of claim 14, wherein the solid or non-porous material is silicone (polydimethylsiloxane), polyurethane or fluoroelastomer.

16. The auricular implant of claim 14, wherein a layer of polytetrafluoroethylene is coated on the outer side of the center model.

17. The auricular implant of claim 1, wherein the supporting member is adhered to the first side of the auricular base via a binder, a suture, or a combination thereof.

18. The auricular implant of claim 1, wherein the spiral member is adhered to the second side of the auricular base via a binder, a suture, or a combination thereof.

* * * * *